United States Patent [19]

Grafelmann

[11] Patent Number: 4,538,304
[45] Date of Patent: Sep. 3, 1985

[54] BONE IMPLANT

[76] Inventor: Hans L. Grafelmann, Parkstrasse 105, D-2800 Bremen 1, Fed. Rep. of Germany

[21] Appl. No.: 666,143

[22] Filed: Oct. 31, 1984

Related U.S. Application Data

[63] Continuation of Ser. No. 448,492, Dec. 10, 1982, abandoned.

[30] Foreign Application Priority Data

Dec. 19, 1981 [DE] Fed. Rep. of Germany ....... 3150490

[51] Int. Cl.³ .............................................. A61F 1/00
[52] U.S. Cl. .................................... 623/16; 433/176; 128/92 C
[58] Field of Search ................................. 3/1, 1.9, 1.91; 128/1 R, 92 C; 433/171, 172, 173, 174, 175, 176

[56] References Cited

U.S. PATENT DOCUMENTS

| 3,465,441 | 9/1967 | Linkow | 433/176 |
| 3,729,825 | 5/1973 | Linkow et al. | 433/176 |
| 3,950,850 | 4/1976 | Driskell et al. | 433/176 |
| 4,164,794 | 8/1979 | Spector et al. | 3/1.9 |
| 4,195,409 | 4/1980 | Child | 433/175 |
| 4,199,824 | 4/1980 | Niederer | 3/1.9 B |
| 4,304,553 | 12/1981 | Heimke et al. | 433/173 |

Primary Examiner—Richard J. Apley
Assistant Examiner—David Isabella
Attorney, Agent, or Firm—Balogh, Osann, Kramer, Dvorak Genova & Traub

[57] ABSTRACT

An improved bone implant for securing artificial teeth to a jaw bone. The implant includes a body plate having an outer end and an inner end and two broadsides, each of which is formed with transversely spaced apart elongated depressions which are transverse to the direction from the outer end to the inner end. Each of the depressions is free from undercut surfaces, and has a longitudinal center plane and is symmetrical with respect to the longitudinal center plane. The depressions may consist of grooves having a semicircular cross-section. The body plate is enlarged in thickness in the shape of a bead at its inner end, in order to promote the application of pressure by the inner end of the body plate to the surrounding body tissue.

3 Claims, 4 Drawing Figures

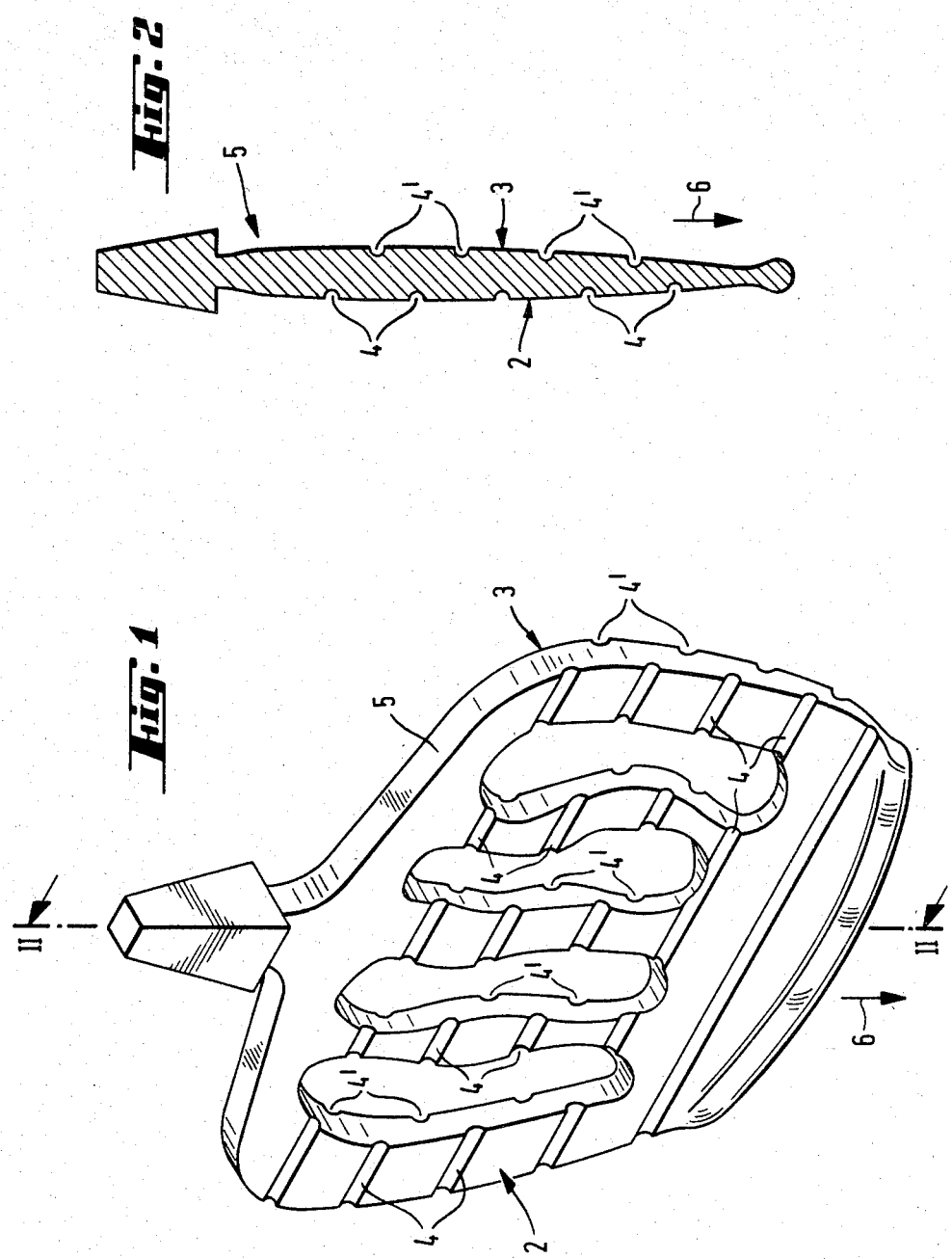

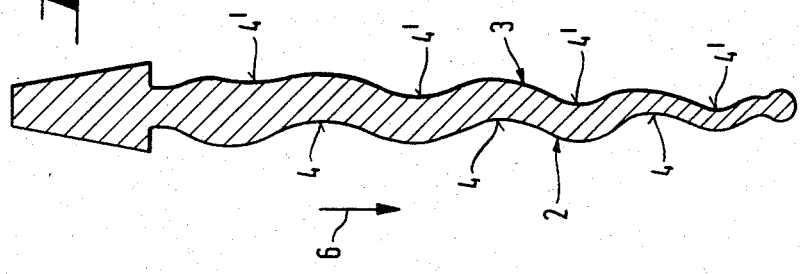
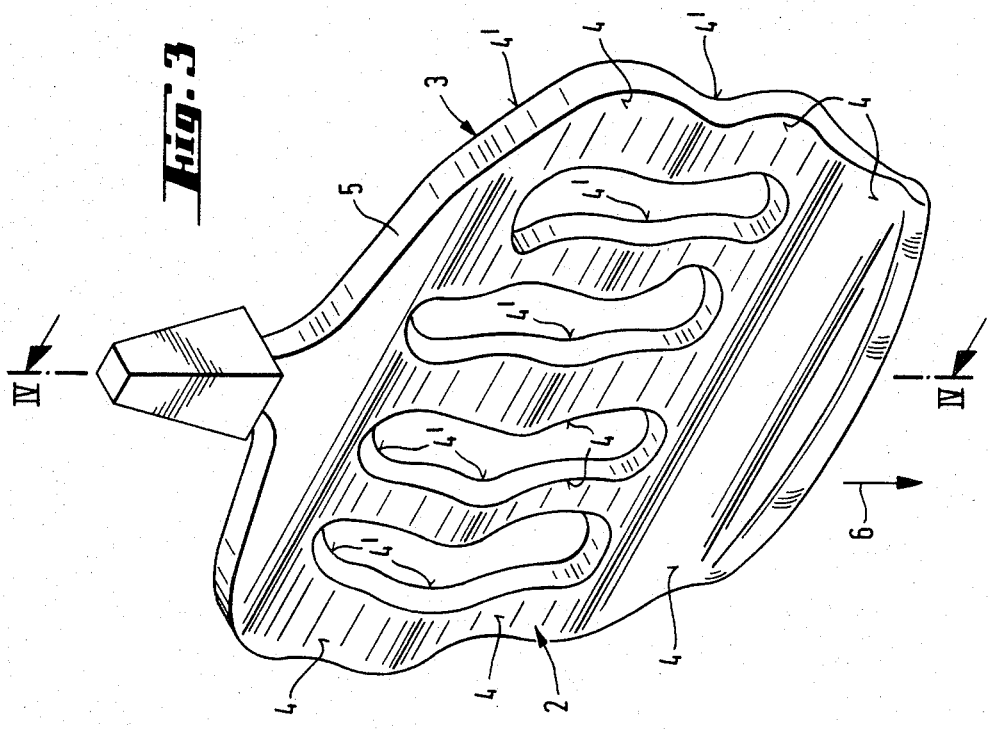

BONE IMPLANT

This application is a continuation of application Ser. No. 448,492, filed Dec. 10, 1982, now abandoned.

BACKGROUND OF THE INVENTION

This invention relates generally to a bone implant and particularly to a bone implant for securing artificial teeth to a jaw bone. For this purpose the body plate and the neck of the implant are inserted into the bone and the tooth is secured to a post carried by the neck and protruding from the bone when the body plate has been inserted into the bone.

Such implants may be made from metal, ceramics or synthetic resin and comprise a body plate, which is wedge-shaped in cross-section or has parallel broadsides and is apertured or non-apertured and is formed with elongated elevations and/or depressions extending on both sides of the body plate transversely to its longitudinal direction, i.e. the direction from the outer end of the body plate to its inner end.

The body plate is inserted into a recess or slit which has previously been formed in the jaw bone by milling, and carries one or two or three posts, which are integral with the body plate. In the known implants, the above-mentioned surface elevations and depressions of the body plate have in cross-section the shape of saw-teeth which point toward or away from the outer end of the body plate. These sawteeth are intended to assist the retaining of the implant as soon as it has been inserted, and to increase the contact surface between the implant and the tissue. But a dentist must repeatedly pull out and re-insert the implant in order to ensure a proper fit, e.g., when the body plate must be deformed or must be deflected with respect to the post or for other changes of the implant. The sawtooth shape of the elevations and depressions has the disadvantage that portions of the body tissue in contact with the implant are torn off whenever the implant is pulled out so that the slit formed in the bone for receiving the implant is enlarged and the friction between the bone and the implant is reduced and is finally lost. As a result, a very large growth of new bone is required to retain the implant and the latter is movable immediately after its insertion until the bone has healed.

SUMMARY OF THE INVENTION

It is an object of the invention so to design the depressions that they afford the advantages which have been described but the above-mentioned disadvantages are not encountered during the fitting of the implant.

This object is accomplished in accordance with the invention in that the depressions consist of grooves. The grooves may have any desired shape in cross-section for instance, the shape of a semicircle, part of an oval, a triangle, or a quadrangle, provided that each groove is symmetrical with respect to its longitudinal center plane and/or has no undercut surface and/or no sharp edge where the groove merges with adjoining surface portions of the body plate. The depth and width of the grooves can also be freely selected.

The amount of bone which must grow into such grooves need not be so large as with a body plate formed with sawtoothlike elevations. As a result, the implant more closely resembles the wedge shape or parallel-sided shape, which promotes the retention of the implant, and its surface is interrupted only by the grooves.

This shape results in a better retention as that obtained with the known implants particularly during the healing of the bone. When the bone has healed, the implant is additionally anchored by bone which has grown into the grooves. The grooves on one surface of the body plate of the implant may suitably be staggered from the grooves on the opposite side of said plate.

A particularly desirable shape of the implant described last will be obtained if the entire body plate is corrugated so that it has a sinuous shape in longitudinal section.

Whereas the body plate of the known implants is sharp-edged at its inner end, the body plate of one embodiment of the invention is enlarged in thickness at its inner end to form an arch-shaped blunt bead extending along the entire length of its inner end. This design will promote the application of pressure by the body plate to the surrounding bone tissue.

BRIEF DESCRIPTION OF THE DRAWINGS

The drawing shows diagrammatically and partly in section a preferred embodiment of the invention with grooves which are semicircular in cross-section. In the drawing FIG. 1 is a perspective view showing an implant embodying the invention, FIG. 2 a sectional view taken on line II—II of FIG. 1, FIG. 3 a perspective view showing an implant having a corrugated body plate and FIG. 4 a sectional view taken on line IV—IV of FIG. 3.

DESCRIPTION OF THE PREFERRED EMBODIMENT

The implant shown in FIGS. 1 and 2 of the drawing comprises a substantially flat body plate 5 and a neck at the outer end of the body plate 5. The neck carries a wedge-shaped post adapted to hold an artificial tooth. The body plate 5 has mutually opposite broadsides 2, 3, which are formed with transversely spaced apart grooves 4, 4', which are semicircular in cross-section and extend transversely to the longitudinal direction of the body plate 5, which is the direction from the outer end to the inner end of the body plate and indicated by the arrow 6. The grooves 4 formed on the broadside 2 are parallel to as well as staggered from the grooves 4' on the broadside 3.

In a preferred embodiment, shown in FIGS. 3 and 4, the body plate 5 is corrugated so that it has a sinuous shape in longitudinal section, as shown in FIG. 4, and the depressions 4, 4' in the broadsides 2 and 3 are defined by the softly curved corrugations of the body plate 5. As shown in FIG. 4, the corrugations formed on each of the broadsides 2 and 3 may be suitably staggered from the corrugations formed on the respectively opposite broadside. FIG. 4 shows also that in thus embodiment the body plate 5 is enlarged in thickness at its inner end to form an arch-shaped blunt bead extending along the entire length of its inner end in order to improve the application of pressure by the inner end of the plate to the surrounding bone tissue.

What is claimed is:

1. In a bone implant for securing artificial teeth to a jaw bone, comprising a substantially flat body plate having an outer end and an inner end and two broadsides, each of which is formed with transversely spaced apart, elongated depressions, which are transverse to the direction from said outer end to said inner end, the improvement comprising said depressions defined by softly curved corrugations merging into adjoining portions of said broadsides without forming a sharp edge therewith and being free of undercut surfaces, so as to facilitate removal of the implant without tearing off body tissue and while retaining existing friction between the jaw bone and the implant, the corrugations formed in one of said two broadsides being staggered from those formed in the other of said two broadsides, each of the corrugations having a longitudinal center plane and being symmetrical with respect to said longitudinal center plane, and the body plate being provided with a plurality of openings closed on all sides thereof, and being enlarged in thickness at said inner end thereof forming an arch-shaped blunt bead extending along the entire length of said inner end thereof, in order to promote the application of pressure by said inner end of the body plate to surrounding body tissue.

2. The improvement set forth in claim 1, wherein said depressions consist of grooves.

3. The improvement set forth in claim 1, wherein said depressions consist of semi-circular grooves.

* * * * *